US010160996B2

(12) United States Patent
Yoshida et al.

(10) Patent No.: US 10,160,996 B2
(45) Date of Patent: Dec. 25, 2018

(54) METHOD AND KIT FOR ANALYZING TARGET

(71) Applicant: NEC Solution Innovators, Ltd., Tokyo (JP)

(72) Inventors: Yoshihito Yoshida, Tokyo (JP); Katsunori Horii, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 82 days.

(21) Appl. No.: 15/023,838

(22) PCT Filed: Jul. 23, 2014

(86) PCT No.: PCT/JP2014/069390
§ 371 (c)(1),
(2) Date: Mar. 22, 2016

(87) PCT Pub. No.: WO2015/045593
PCT Pub. Date: Apr. 2, 2015

(65) Prior Publication Data
US 2016/0230212 A1    Aug. 11, 2016

(30) Foreign Application Priority Data

Sep. 30, 2013 (JP) .................. 2013-205051

(51) Int. Cl.
| C12Q 1/68 | (2018.01) |
| C07H 21/00 | (2006.01) |
| G01N 33/53 | (2006.01) |
| C12Q 1/6806 | (2018.01) |
| C12Q 1/6804 | (2018.01) |
| C12Q 1/6834 | (2018.01) |

(52) U.S. Cl.
CPC ......... C12Q 1/6806 (2013.01); C12Q 1/6804 (2013.01); C12Q 1/6834 (2013.01)

(58) Field of Classification Search
CPC .......... C12Q 1/68; C07H 21/00; C12N 15/11; C12N 15/115
See application file for complete search history.

(56) References Cited

U.S. PATENT DOCUMENTS

| 2003/0134349 A1* | 7/2003 | Ma ....................... C12N 9/1252 435/69.1 |
| 2006/0088864 A1 | 4/2006 | Smolke et al. |
| 2006/0240431 A1 | 10/2006 | Fu |
| 2008/0188375 A1* | 8/2008 | Neri ....................... C12Q 1/6823 506/9 |
| 2008/0233588 A1* | 9/2008 | Squirrell ............. C12Q 1/6816 435/6.15 |
| 2012/0035065 A1 | 2/2012 | Smolke et al. |
| 2013/0274135 A1* | 10/2013 | Zhang .................. C12Q 1/6832 506/9 |
| 2015/0024954 A1 | 1/2015 | Smolke et al. |

FOREIGN PATENT DOCUMENTS

| CN | 1653175 A | 8/2005 |
| CN | 101072874 A | 11/2007 |
| CN | 102918147 A | 2/2013 |
| JP | 2006-508677 A | 3/2006 |
| JP | 2008-515405 A | 5/2008 |
| WO | WO-2003/073067 A2 | 9/2003 |
| WO | WO-20041053159 A2 | 6/2004 |
| WO | WO-2006/042112 A2 | 4/2006 |
| WO | WO-2006/086669 A2 | 8/2006 |
| WO | WO-2011/149255 A2 | 12/2011 |

OTHER PUBLICATIONS

Sakakibara et al., An Enzymatic Cycling Method Using Pyruvate Orthophosphate Dikinase and Firefly Luciferase for the Simultaneous Determination of ATP and AMP (RNA). Analytical Biochemistry 268: 94 (1999).*
International Search Report corresponding to PCT/JP2014/069390, dated Oct. 28, 2014, 1 page.
Carsten, Teller et al., "Aptamer-DNAzyme Hairpins for Amplified Biosensing", Analytical Chemistry, vol. 81, No. 21, Nov. 1, 2009, pp. 9114-9119.
Chinese Office Action issued by The State Intellectual Property Office of People's Republic of China for Chinese Application No. 201480053502.9 dated Jun. 13, 2018 (14 pages).

* cited by examiner

Primary Examiner — Ethan C Whisenant
(74) Attorney, Agent, or Firm — Wilmer Cutler Pickering Hale and Dorr LLP

(57) ABSTRACT

The present invention provides a novel method that can analyze a target easily utilizing binding nucleic acid molecules and an analysis kit for use in the method. The analysis method of the present invention includes: a complex formation step of causing a binding nucleic acid molecule that binds to the target and a sample to come into contact with each other to form a complex of the binding nucleic acid molecule and the target in the sample; a nuclease treatment step of releasing a nucleic acid monomer from at least one of a complex fraction and a non-complex fraction by a nuclease treatment; an enzyme treatment step of reacting the released nucleic acid monomer with an enzyme for which the nucleic acid monomer is a substrate; a detection step of detecting the enzyme reaction; and an analysis step of analyzing the target that has formed the complex from the result of detecting the enzyme reaction.

37 Claims, 7 Drawing Sheets
Specification includes a Sequence Listing.

SEQUENCE LISTING

```
<160> NUMBER OF SEQ ID NOS: 2

<210> SEQ ID NO 1
<211> LENGTH: 79
<212> TYPE: DNA
<213> ORGANISM: Artificial Sequence
<220> FEATURE:
<223> OTHER INFORMATION: nuleic acid molecule
<220> FEATURE:
<221> NAME/KEY: misc_feature
<222> LOCATION: (25)..(54)
<223> OTHER INFORMATION: n is a, c, g, or t

<400> SEQUENCE: 1
ggattgaacg ccgcccttat aaacnnnnnn nnnnnnnnnn nnnnnnnnnn nnnncatcag      60
gtccagtgct ctcgtatag                                                  79

<210> SEQ ID NO 2
<211> LENGTH: 67
<212> TYPE: DNA
<213> ORGANISM: Artificial Sequence
<220> FEATURE:
<223> OTHER INFORMATION: aptamer

<400> SEQUENCE: 2
gggtttgggt tgggttgggt ttttgggttt gggttgggtt gggaaaaaaa aaaaaaaaaa      60
aaaaaaa                                                               67
```

METHOD AND KIT FOR ANALYZING TARGET

CROSS-REFERENCE TO RELATED APPLICATIONS

This application is a national stage application of International Application No. PCT/JP2014/069390 entitled "METHOD AND KIT FOR ANALYZING TARGET," filed on Jul. 23, 2014, which claims the benefit of the priority of Japanese Patent Application No. 2013-205051 filed on Sep. 30, 2013, the disclosures of each of which are hereby incorporated by reference in their entirety.

TECHNICAL FIELD

The present invention relates to a method and a kit for analyzing a target.

BACKGROUND ART

In recent years, attempts have been made to carry out target detection utilizing a sensor including, instead of antibodies that bind specifically to a target, binding nucleic acid molecules (a so-called "aptamers") that bind specifically to the target. As such a sensor, there has been reported a sensor configured so that DNA having an ability to catalyze a redox reaction (referred to as "DNAzyme" hereinafter) is linked to binding nucleic acid molecules in order to examine the binding of a target to the binding nucleic acid molecules (Non-Patent Document 1), for example. In this sensor, self-association of the binding nucleic acid molecules and the DNAzyme occurs in the absence of the target, whereby the catalytic ability of the DNAzyme is inhibited (OFF). On the other hand, in the presence of the target, the self-association is released by the contact of the target with the aptamers, whereby the catalytic ability of the DNAzyme is activated (ON). Thus, if the target is present, the DNAzyme with its catalytic ability being activated causes a redox reaction, so that the target can be analyzed indirectly by measuring the reaction.

However, the above-described sensor requires ON-OFF control of the catalytic ability of the DNAzyme used in the sensor, depending on the presence or absence of the target. Also, in order to further improve the analytical sensitivity in the analysis using the sensor, it is necessary to use a DNAzyme exhibiting a stronger catalytic ability, for example.

ELAA (Enzyme-linked Aptamer Assay) using binding nucleic acid molecules (aptamers) is a method using binding nucleic acid molecules labeled with biotin, for example. In this method, an enzyme, such as horseradish peroxidase or alkaline phosphatase, fused with streptavidin is bound to the biotin-labeled nucleic acid molecules, and binding of a target to the binding nucleic acid molecules is analyzed by detecting the substrate for the enzyme. However, in ELAA, labeling of the binding nucleic acid molecules is essential, and in order to further improve the analytical sensitivity, it is necessary to improve various condition settings, for example.

As described above, in the case where the above-described sensor is used, it is necessary to make various improvements in order to perform more reliable analysis.

Under these circumstances, there are demands for a method that can detect a target easily using binding nucleic acid molecules and also can improve the analytical sensitivity easily.

CITATION LIST

Non-Patent Document(s)

[Non-Patent Document 1] Carsten Teller et al., Anal. Chem. 2009, 81, pp. 9114-9119

BRIEF SUMMARY OF THE INVENTION

Problem to be Solved by the Invention

With the foregoing in mind, it is an object of the present invention to provide a novel method that can analyze a target easily utilizing binding nucleic acid molecules and an analysis kit for use in the method.

Means for Solving Problem

The present invention provides an analysis method for analyzing a target, including: a complex formation step of causing a binding nucleic acid molecule that binds to the target and a sample to come into contact with each other to form a complex of the binding nucleic acid molecule and the target in the sample; a nuclease treatment step of releasing a nucleic acid monomer from at least one of a complex fraction and a non-complex fraction by a nuclease treatment; an enzyme treatment step of reacting the released nucleic acid monomer with an enzyme for which the nucleic acid monomer is a substrate; a detection step of detecting the enzyme reaction; and an analysis step of analyzing the target that has formed the complex from the result of detecting the enzyme reaction.

The present invention also provides an analysis kit for use in the analysis method according to the present invention, including: a binding nucleic acid molecule that binds to a target; a nuclease; and an enzyme for which a nucleic acid monomer is a substrate.

Effects of the Invention

According to the analysis method of the present invention, it is possible to detect a target easily by forming complexes of the target and the binding nucleic acid molecules, releasing nucleic acid monomers from a complex fraction or a non-complex fraction, and performing an enzyme reaction with the released nucleic acid monomers as a substrate. According to this method, for example, it is not necessary to link a DNAzyme to aptamers as described above, so that the ON-OFF control of the catalytic ability of the DNAzyme depending on the presence or absence of a target also is not necessary. Also, according to the analysis kit of the present invention, the analysis method of the present invention can be carried out easily. Because the present invention relates to a target detection method using aptamers, it can be said that the present invention is a very useful technique for research and tests in various fields such as clinical medical practice, foods, and environments, for example.

MODE FOR CARRYING OUT THE INVENTION

Figure 1A:
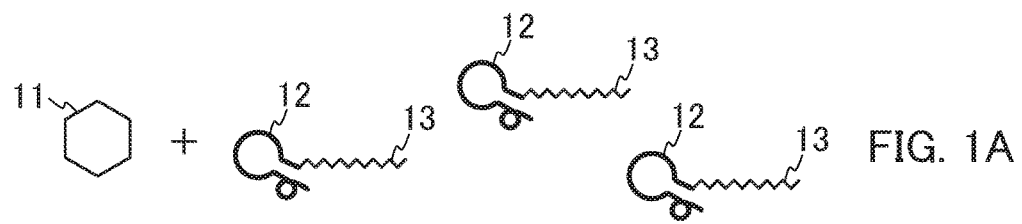
FIG. 1 is a schematic view showing an example of the analysis method of the present invention.
Figure 1B:
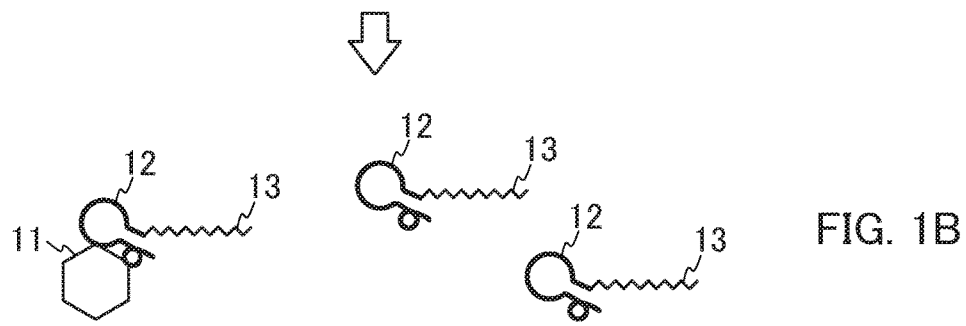
Figure 1C:
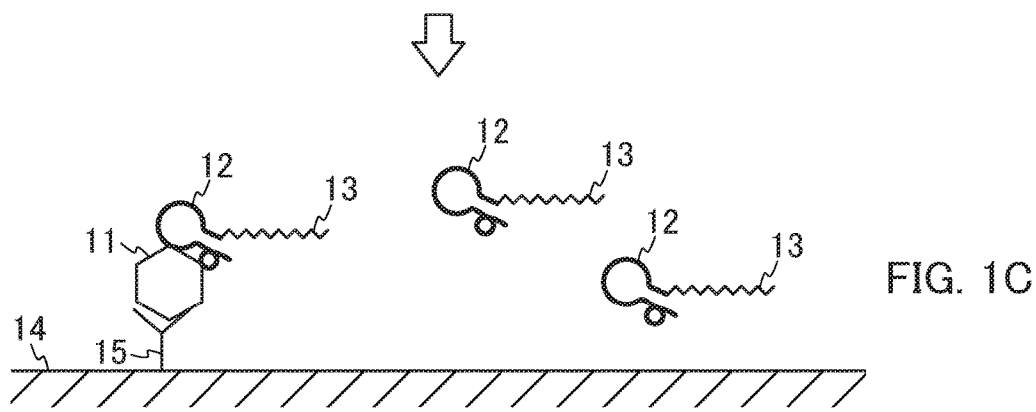
Figure 1D:
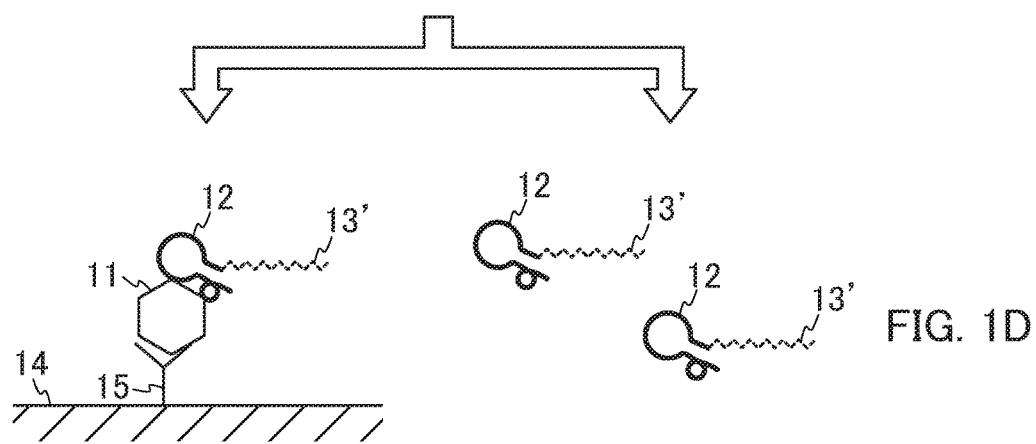
Figure 2A:
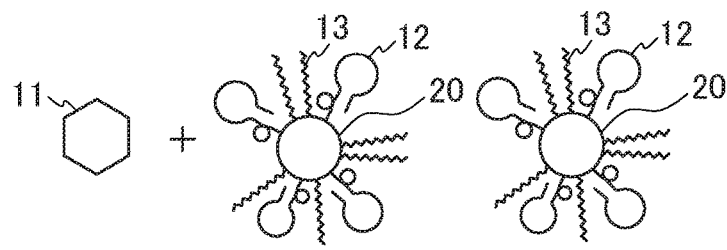
FIG. 2 is a schematic view showing another example of the analysis method of the present invention.
Figure 2B:
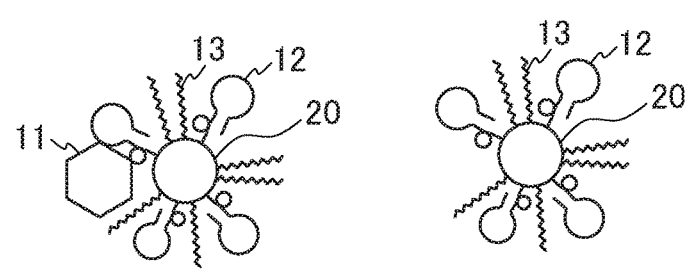
Figure 2C:
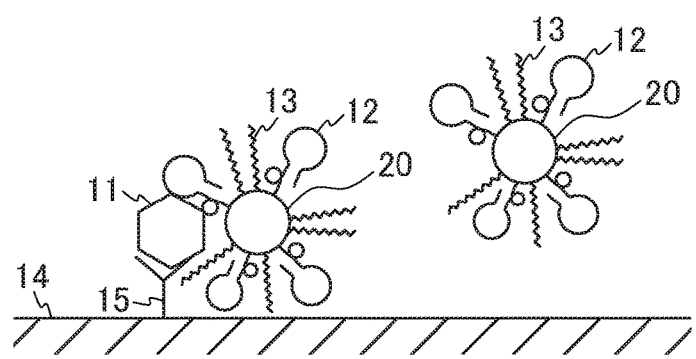
Figure 2D:
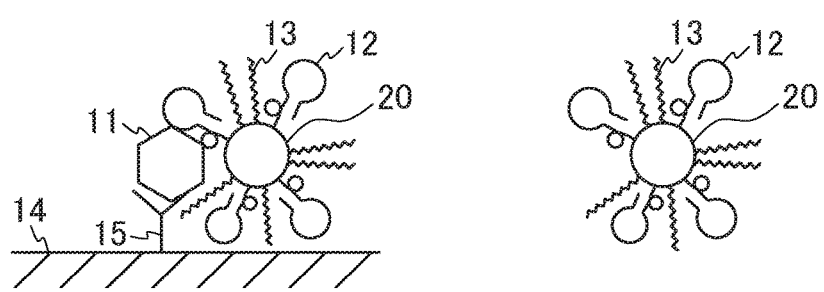

As described above, the analysis method of the present invention is an analysis method for analyzing a target, including: a complex formation step of causing a binding nucleic acid molecule that binds to the target and a sample to come into contact with each other to form a complex of the binding nucleic acid molecule and the target in the sample; a nuclease treatment step of releasing a nucleic acid monomer from at least one of a complex fraction and a non-complex fraction by a nuclease treatment; an enzyme treatment step of reacting the released nucleic acid monomer with an enzyme for which the nucleic acid monomer is a substrate; a detection step of detecting the enzyme reaction; and an analysis step of analyzing the target that has formed the complex from the result of detecting the enzyme reaction.

The analysis method of the present invention may be configured so that, for example, it further includes, after the complex formation step, a separation step of separating the complex fraction and the non-complex fraction from a reaction system for the complex formation.

The analysis method of the present invention may be configured so that, for example, in the separation step, the complex fraction and the non-complex fraction are separated by causing the reaction system for the complex formation and an immobilized binding substance to come into contact with each other to bind the complex to the binding substance, and the binding substance is a binding substance that binds to the target.

The analysis method of the present invention may be configured so that, for example, in the separation step, after the complex has been bound to the binding substance, the immobilized binding substance is washed to remove an unreacted binding nucleic acid molecule.

The analysis method of the present invention may be configured so that, for example, in the nuclease treatment step, the complex fraction is subjected to the nuclease treatment to release the nucleic acid monomer from the complex.

The analysis method of the present invention may be configured so that, for example, in the nuclease treatment step, the non-complex fraction is subjected to the nuclease treatment to release the nucleic acid monomer from an unreacted binding nucleic acid molecule.

The analysis method of the present invention may be configured so that, for example, the binding nucleic acid molecule includes a polynucleotide added thereto, and the polynucleotide includes a nucleic acid monomer that is the substrate for the enzyme.

The analysis method of the present invention may be configured so that, for example, the binding nucleic acid molecule is carried on a carrier.

The analysis method of the present invention may be configured so that, for example, the carrier further includes a polynucleotide added thereto, and the polynucleotide includes a nucleic acid monomer that is the substrate for the enzyme.

The analysis method of the present invention may be configured so that, for example, in the nuclease treatment step, the reaction system in the complex formation step is subjected to the nuclease treatment to release the nucleic acid monomer from an unreacted binding nucleic acid molecule.

The analysis method of the present invention may be configured so that, for example: the binding nucleic acid molecule is in a form of a hybrid with a single-stranded nucleic acid molecule including a sequence complementary to the binding nucleic acid molecule; in the complex formation step, the hybrid and the sample are caused to come into contact with each other to form a complex of the binding nucleic acid molecule in the hybrid and the target and to release the single-stranded nucleic acid molecule from the hybrid; and in the nuclease treatment step, the reaction system in the complex formation step is subjected to the nuclease treatment to release the nucleic acid monomer from the released single-stranded nucleic acid molecule.

The analysis method of the present invention may be configured so that, for example: the binding nucleic acid molecule is carried on a carrier and is in a form of a hybrid with a single-stranded nucleic acid molecule including a sequence complementary to the binding nucleic acid molecule; in the complex formation step, the hybrid and the sample are caused to come into contact with each other to form a complex of the binding nucleic acid molecule in the hybrid and the target and to release the single-stranded nucleic acid molecule from the hybrid; and in the nuclease treatment step, the reaction system in the complex formation step is subjected to the nuclease treatment to release the nucleic acid monomer from the released single-stranded nucleic acid molecule.

The analysis method of the present invention may be configured so that, for example, it further includes, after the complex formation step, a separation step of separating the released single-stranded nucleic acid molecule from a reaction system in the complex formation step, and in the nuclease treatment step, the separated single-stranded nucleic acid molecule is subjected to the nuclease treatment to release the nucleic acid monomer from the single-stranded nucleic acid molecule.

The analysis method of the present invention may be configured so that, for example, the nuclease is a nuclease for which the single-stranded nucleic acid molecule is a substrate.

The analysis method of the present invention may be configured so that, for example, the nuclease is an exonuclease.

The analysis method of the present invention may be configured so that, for example, the nucleic acid monomer as a substrate for the enzyme is an adenosine nucleotide, which may be, for example, at least one of ribonucleotide and deoxyribonucleotide.

The analysis method of the present invention may be configured so that, for example, the enzyme is a protein having luciferase activity, and a specific example thereof is luciferase.

The analysis method of the present invention may be configured so that, for example, in the enzyme treatment step, the enzyme reaction is performed in the presence of a reagent, and the reagent is a reagent that causes a signal to be generated by an enzyme reaction with the nucleic acid monomer as a substrate or a reagent that causes a signal to disappear by an enzyme reaction with the nucleic acid monomer as a substrate.

The analysis method of the present invention may be configured so that, for example, in the detection step, a signal generated by the enzyme reaction or a signal caused to disappear by the enzyme reaction is detected.

The analysis method of the present invention may be configured so that, for example, the signal is at least one of an optical signal and an electrical signal.

The analysis method of the present invention may be configured so that, for example, the carrier is a bead or a plate.

The analysis kit of the present invention is, for example, an analysis kit for use in the analysis method according to the present invention, including: a binding nucleic acid molecule that binds to a target; a nuclease; and an enzyme for which a nucleic acid monomer is a substrate.

The analysis kit of the present invention may be configured so that, for example, the binding nucleic acid molecule includes a polynucleotide added thereto, and the polynucleotide includes a nucleic acid monomer that is the substrate for the enzyme.

The analysis kit of the present invention may be configured so that, for example, the binding nucleic acid molecule is carried on a carrier.

The analysis kit of the present invention may be configured so that, for example, the carrier further includes a polynucleotide added thereto, and the polynucleotide includes a nucleic acid monomer that is the substrate for the enzyme.

The analysis kit of the present invention may be configured so that, for example, the binding nucleic acid molecule is in a form of a hybrid with a single-stranded nucleic acid molecule including a sequence complementary to the binding nucleic acid molecule, and through contact with the target, the binding nucleic acid molecule in the hybrid forms a complex with the target and the single-stranded nucleic acid molecule is released.

The analysis kit of the present invention may be configured so that, for example, the nuclease is a nuclease for which the single-stranded nucleic acid molecule is a substrate.

The analysis kit of the present invention may be configured so that, for example, the binding nucleic acid molecule is carried on a carrier and is in a form of a hybrid with a single-stranded nucleic acid molecule including a sequence complementary to the binding nucleic acid molecule, and through contact with the target, the binding nucleic acid molecule in the hybrid forms a complex with the target and the single-stranded nucleic acid molecule is released.

The analysis kit of the present invention may be configured so that, for example, the nuclease is an exonuclease.

The analysis kit of the present invention may be configured so that, for example, the nucleic acid monomer as a substrate for the enzyme is an adenosine nucleotide, which may be, for example, at least one of ribonucleotide and deoxyribonucleotide.

The analysis kit of the present invention may be configured so that, for example, the enzyme is a protein having luciferase activity, and a specific example thereof is luciferase.

The analysis kit of the present invention may be configured so that, for example, it further includes a reagent, and the reagent is a reagent that causes a signal to be generated by an enzyme reaction with the monomer as a substrate or a reagent that causes a signal to disappear by an enzyme reaction with the monomer as a substrate.

The analysis kit of the present invention may be configured so that, for example, the signal is at least one of an optical signal and an electrical signal.

The analysis kit of the present invention may be configured so that, for example, the carrier is a bead or a plate.

(Target Analysis Method)

As described above, the target analysis method of the present invention is an analysis method for analyzing a target, including: a complex formation step of causing a binding nucleic acid molecule that binds to the target and a sample to come into contact with each other to form a complex of the binding nucleic acid molecule and the target in the sample; a nuclease treatment step of releasing a nucleic acid monomer from at least one of a complex fraction and a non-complex fraction by a nuclease treatment; an enzyme treatment step of reacting the released nucleic acid monomer with an enzyme for which the nucleic acid monomer is a substrate; a detection step of detecting the enzyme reaction; and an analysis step of analyzing the target that has formed the complex from the result of detecting the enzyme reaction. In the present invention, the term "analysis" is a concept encompassing quantitative analysis, semi-quantitative analysis, and qualitative analysis, for example.

In the complex formation step, the binding nucleic acid molecule is not particularly limited, as long as it binds to the target. The binding nucleic acid molecule also is referred to as an aptamer, for example.

The target is not particularly limited, and any target can be selected. Then, depending on the selected target, the binding nucleic acid molecule that binds to the target may be used. Examples of the target include microorganisms, viruses, low molecular weight compounds, food allergens, agricultural chemicals, and mycotoxins.

The binding nucleic acid molecule may be either a single strand or a double strand, for example, and preferably is a single strand. The length of the binding nucleic acid molecule is not particularly limited. The lower limit thereof is, for example, 18, 20, or 24 in base length, and the upper limit thereof is, for example, 120, 60, or 26 in base length.

In the complex formation step, the sample is not particularly limited. The sample may be either a sample containing a target or a sample for which the presence or absence of a target is unknown, for example. Preferably, the sample is a liquid sample, for example.

In the nuclease treatment step, for example, only the complex fraction may be subjected to the nuclease treatment, only the non-complex fraction may be subjected to the nuclease treatment, or the reaction system in the complex formation step (i.e., a mixed system containing the complex fraction and the non-complex fraction) may be subjected to the nuclease treatment.

In the case where only the complex fraction or only the non-complex fraction is subjected to the nuclease treatment, it is preferable that the present invention includes, after the complex formation step and prior to the nuclease treatment step, a separation step of separating the complex fraction and the non-complex fraction from the reaction system for the complex formation.

The method for separating the complex fraction and the non-complex fraction is not particularly limited. For example, the complex fraction and the non-complex fraction can be separated by binding the complexes with a carrier(s) and collecting the complex fraction by collecting the carrier(s). The carrier and the complexes may be bound to each other directly, or they may be bound to each other indirectly, for example. In the former case, the carrier(s) adapted to carry the binding nucleic acid molecules in advance can be used, for example. In this case, complexes of the binding nucleic acid molecules carried on the carrier(s) and the target are formed, whereby the complexes can be bound to the carrier(s) directly. In the latter case, the carrier(s) carrying binding substances that bind to the target can be used, for example. In this case, complexes of the target and the binding nucleic acid molecules are formed, and the binding nucleic acid molecules in the complexes bind to the binding substances carried on the carrier(s), whereby the complexes can be bound to the carrier(s) indirectly via the binding substances.

The carrier is not particularly limited, and may be, for example, a bead or a container such as a plate. The binding substance is not particularly limited, and examples thereof include binding nucleic acid molecules and antibodies against the above-described binding nucleic acid molecules.

When the carrier is used, the method for separating the complex fraction and the non-complex fraction is not particularly limited, and examples thereof include solid-liquid separation. When a container is used as the carrier, by collecting a liquid fraction from the container, the remaining fraction in the container can be provided as the complex fraction and the collected liquid fraction can be provided as the non-complex fraction. When beads are used as the carriers, by separating the reaction system into a solid fraction and a liquid fraction, the former can be provided as the complex fraction and the latter can be provided as the non-complex fraction. The separation of the solid fraction and the liquid fraction can be achieved by filtration, centrifugation, still standing, or the like, for example.

In the case where the present invention includes the separation step and the complex fraction is subjected to the nuclease treatment, the present invention may further include, between the separation step and the nuclease treatment step, the step of washing the complex fraction, for example. By washing the complex fraction, it becomes possible to inhibit the contamination with unreacted binding nucleic acid molecules that have not been involved in the complex formation, whereby analysis with still higher accuracy becomes possible, for example.

In the nuclease treatment step, the nuclease is not particularly limited, as long as it is an enzyme that releases nucleic acid monomers from a polynucleotide. The nuclease preferably is an exonuclease that releases nucleic acid monomers from an end of the polynucleotide, for example. The release of the nucleic acid monomer may be initiated either from the 3' end or the 5' end of the polynucleotide. Examples of the exonuclease include snake venom nuclease, spleen phosphodiesterase, RNase H, BAL31, Exonuclease I, Exonuclease III, Exonuclease VII, and λ exonuclease. The nuclease may be, for example, any of a ribonuclease acting on RNA, a deoxyribonuclease acting on DNA, or a nuclease acting on both RNA and DNA.

The nucleic acid monomer to be cleaved by the nuclease is not particularly limited, and may be a nucleotide residue, for example. The sugar residue in the nucleotide residue may be either a ribose residue or a deoxyribose residue, for example. When the sugar residue is a ribose residue, the nucleotide residue is a ribonucleotide residue. When the sugar residue is a deoxyribose residue, the nucleotide residue is a deoxyribonucleotide residue. The base in the nucleotide residue is not particularly limited, and examples thereof include adenine, guanine, cytosine, thymine, and uracil. The phosphate group in the nucleotide residue is not particularly limited, and may be monophosphate or diphosphate, for example. Specific examples of the nucleic acid monomer include AMP and deoxy-AMP (dAMP).

In the enzyme treatment step, the enzyme is not particularly limited, as long as it is a protein that catalyzes a reaction with the nucleic acid monomers as a substrate. The enzyme is not particularly limited, and may be, for example, a protein having luciferase activity, and preferably is luciferase.

The enzyme can be set as appropriate depending on the kind of the nucleic acid monomers to be cleaved in the nuclease treatment step, for example.

In the enzyme treatment step, the enzyme reaction may be performed in the presence of a reagent, for example. The reagent may be, for example, a reagent that causes a signal to be generated by an enzyme reaction with the nucleic acid monomers as a substrate or a reagent that causes a signal to disappear by an enzyme reaction with the nucleic acid monomers as a substrate. The signal may be an optical signal or an electrical signal, for example.

The order of performing the nuclease treatment step and the enzyme treatment step is not particularly limited. The enzyme treatment step may be performed after the nuclease treatment step, or both the steps may be performed at the same time.

It is preferable that the analysis method of the present invention further include the step of converting the nucleic acid monomers cleaved in the nuclease treatment step into nucleotides in which the phosphate groups are triphosphate, for example. Specifically, when the nuclease treatment step, nucleotides with monophosphate or diphosphate are cleaved as the nucleic acid monomers, the nucleic acid monomers are converted to nucleotides with triphosphate in the converting treatment step, for example. When the analysis method further includes the converting treatment step, the sensitivity can be further improved.

In the converting treatment step, conversion to the nucleotides with triphosphate can be achieved using, for example, a converting enzyme for converting nucleotides with monophosphate or diphosphate to nucleotides with triphosphate. The converting enzyme is not particularly limited, and examples thereof include pyruvate orthophosphate dikinase.

When the nucleic acid monomers are converted to nucleotides with triphosphate in the converting treatment step, it is preferably to use an enzyme for which the nucleotides with triphosphate are a substrate in the enzyme treatment step. As the enzyme for which the nucleotides with triphosphate are a substrate, luciferase or the like can be used, for example.

The order of performing the nuclease treatment step, the converting treatment step, and the enzyme treatment step is not particularly limited. They may be performed in this order; the nuclease treatment step and the converting treatment step may be performed at the same time; the converting treatment step and the enzyme treatment step may be performed at the same time; or these three steps may be performed at the same time.

In the detection step, detection of an enzyme reaction caused by the enzyme is not particularly limited. The detection can be achieved by, for example, detecting the decrease in the substrate by the enzyme reaction directly or indirectly. The indirect detection is, for example, detection of a signal generated by the enzyme reaction. As a specific example, the signal may be a signal generated from the reagent by the enzyme reaction, for example. The signal may be an optical signal or an electrical signal, for example.

The optical signal may be, for example, a signal such as light emission, fluorescence, color development, or the like. The optical signal may be detected by visual observation of light emission, fluorescence, color development, or the like, for example. Alternatively, the light emission intensity, fluorescence intensity, absorbance, reflectance, or the like may be detected as a signal by an optical method.

The electrical signal may be a current or the like, for example. The electrical signal can be detected by an electrical method, for example.

The analysis step is the step of analyzing the target contained in the complex fraction from the result of detecting the enzyme reaction in the detection step. The result of detecting the enzyme reaction may be, for example, the result of detecting the enzyme reaction performed with respect to the complex fraction, the enzyme reaction performed with respect to the non-complex fraction, or the enzyme reaction performed with respect to the reaction system in the complex formation step (i.e., a mixed system containing the complex fraction and the non-complex fraction).

The analysis method of the present invention will be described below with reference to, as specific examples, Embodiment 1 where the complex fraction and the non-complex fraction are separated, Embodiment 2 where the two fractions are not separated, and Embodiment 3 where hybrids each composed of the binding nucleic acid molecule and a single-stranded nucleic acid molecule including a sequence complementary to the binding nucleic acid molecule are used. It is to be noted, however, that the present invention is by no means limited to these exemplary embodiments. Unless otherwise stated, the description in each of the embodiments also is applicable to the other embodiments.

(1) Embodiment 1

As described above, Embodiment 1 of the present invention is directed to an aspect where, after the complex formation step, the complex fraction and the non-complex fraction are separated from the reaction system in the complex formation step. For instance, Embodiments 1A, 1B, and 1C to be described below can be given as examples.

First, Embodiment 1A of the present invention is directed to an aspect where the complex fraction is subjected to the nuclease treatment. Specifically, the analysis method of Embodiment 1A includes: a complex formation step of causing binding nucleic acid molecules that bind to a target and a sample to come into contact with each other to form complexes of the binding nucleic acid molecules and the target in the sample; a separation step of separating a complex fraction and a non-complex fraction from a reaction system for the complex formation; a nuclease treatment step of releasing nucleic acid monomers from the complex fraction by a nuclease treatment; an enzyme treatment step of reacting the released nucleic acid monomers with an enzyme for which the nucleic acid monomers are a substrate; a detection step of detecting the enzyme reaction; and an analysis step of analyzing the target that has formed the complexes from the result of detecting the enzyme reaction.

In Embodiment 1A, the complex fraction and the non-complex fraction are separated. Thus, in the nuclease treatment step, nucleic acid monomers are released from the binding nucleic acid molecules in the complexes, and in the enzyme treatment step, an enzyme reaction is caused with the released nucleic acid monomers as a substrate. Thus, the result of detecting the enzyme reaction in the detection step corresponds to the result of detecting the complexes, and thus indirectly indicates the result of detecting the target contained in the complexes.

In Embodiment 1A, as the binding nucleic acid molecule, it is preferable to use a binding nucleic acid molecule to which a polynucleotide (also referred to as "addition polynucleotide" hereinafter) has been added. By using the binding nucleic acid molecule to which the polynucleotide has been added, for example, it is possible to increase the number of nucleic acid monomers released from the binding nucleic acid molecule in the complex. Because the released nucleic acid monomers serve as a substrate in the enzyme treatment step, the detection sensitivity can be improved further as the number of the released nucleic acid monomers increases.

The polynucleotide added to the binding nucleic acid molecule is not particularly limited. The lower limit of the length of the addition polynucleotide is, for example, 0 bases, 10 bases, or 20 bases, and the upper limit of the same is, for example, 1000 bases, 200 bases, or 20 bases.

The kind of nucleic acid monomers constituting the addition polynucleotide is not particularly limited, and can be determined as appropriate depending on the substrate specificity of an enzyme to be used in the enzyme treatment step, for example. In the addition polynucleotide, the nucleic acid monomers are linked with each other via phosphodiester linkage, for example. The nucleic acid monomer is a nucleotide residue, for example. The sugar residue in the nucleotide residue may be either a ribose residue or a deoxyribose residue, for example. When the sugar residue is a ribose residue, the nucleotide residue is a ribonucleotide residue. When the sugar residue is a deoxyribose residue, the nucleotide residue is a deoxyribonucleotide residue. The base in the nucleotide residue is not particularly limited, and examples thereof include adenine, guanine, cytosine, thymine, and uracil. The phosphate group in the nucleotide residue is not particularly limited, and may be monophosphate, diphosphate, or triphosphate, for example. Specific examples of the nucleic acid monomer include AMP and deoxy-AMP (dAMP). The addition polynucleotide may be constituted by one kind or two or more kinds of nucleotide residues, for example. In particular, it is preferable that the addition polynucleotide is constituted by at least one of AMP and deoxy-AMP (dAMP). It is more preferable that the addition polynucleotide is constituted by either one kind of nucleotide residue selected from AMP and deoxy-AMP (dAMP).

The addition polynucleotide may be added to the 3' end or the 5' end of the binding nucleic acid molecule, for example. The position at which the addition polynucleotide is added in the binding nucleic acid molecule can be determined as appropriate depending on the properties of the nuclease, for example. In the case where the nuclease releases the nucleic acid monomers from the 5' end toward the 3' end, for example, the addition polynucleotide preferably is added to the 5' end of the binding nucleic acid molecule. In the case where the nuclease releases the nucleic acid monomers from the 3' end toward the 5' end, for example, the addition polynucleotide preferably is added to the 3' end of the binding nucleic acid molecule.

Regarding Embodiment 1A, an example where binding nucleic acid molecules each having the addition polynucleotide added thereto are used will be described with reference to FIG. 1. FIG. 1 is a schematic view showing the outline of Embodiment 1A of the present invention, and (A) to (D) show the respective steps. It is to be noted that FIG. 1 is a schematic view, and the conditions such as the sizes of a target, binding nucleic acid molecules, addition polynucleotides, and the like, are not limited to those shown in FIG. 1, for example.

First, in the complex formation step, as shown in (A) in FIG. 1, a sample containing a target 11 is brought into contact with binding nucleic acid molecules 12 each having the addition polynucleotide 13. As a result, as shown in (B) in FIG. 1, in a reaction solution in the complex formation step, complexes are formed by the target 11 in the sample and the binding nucleic acid molecules 12 each having the addition polynucleotide 13. At this time, unreacted binding nucleic acid molecules 12 that have not been involved in the complex formation also are present in the reaction solution.

Then, in the separation step, as shown in (C) in FIG. 1, the reaction solution is brought into contact with binding substances 15 immobilized on a carrier 14. The binding substances 15 are substances that bind to the target 11. Thus, as shown in (C) in FIG. 1, the complexes contained in the reaction solution bind to the carrier 14 via the binding between the target 11 and the binding substances 15. At this time, the unreacted binding nucleic acid molecules 12 do not bind to the carrier 14, and they are present in a free state in the reaction solution.

Next, the reaction solution is treated so as to separate the carrier 14 to which the complexes have been bound and the fraction other than the carrier 14. Specifically, for example, the liquid fraction is removed from the carrier 14. Then, a nuclease treatment is performed by adding a nuclease to the carrier 14. By the nuclease treatment, as shown on the left in (D) in FIG. 1, the addition polynucleotides 13 in the complexes bound to the carrier 14 are degraded, whereby nucleic acid monomers 13' are cleaved.

Then, the nucleic acid monomers 13' cleaved from the addition polynucleotides 13 are treated with an enzyme for which the nucleic acid monomers are a substrate, and the enzyme reaction is detected. Thus, the target in the sample can be analyzed.

Next, Embodiment 1B of the present invention is directed to an aspect where the non-complex fraction is subjected to the nuclease treatment. Specifically, the analysis method of Embodiment 1B includes: a complex formation step of causing binding nucleic acid molecules that bind to a target and a sample to come into contact with each other to form complexes of the binding nucleic acid molecules and the target in the sample; a separation step of separating a complex fraction and a non-complex fraction from a reaction system for the complex formation; a nuclease treatment step of releasing nucleic acid monomers from the non-complex fraction by a nuclease treatment; an enzyme treatment step of reacting the released nucleic acid monomers with an enzyme for which the nucleic acid monomers are a substrate; a detection step of detecting the enzyme reaction; and an analysis step of analyzing the target that has formed the complexes from the result of detecting the enzyme reaction.

The analysis method of Embodiment 1B can be carried out in the same manner as the analysis method of Embodiment 1A, except that: the addition polynucleotide may or may not be added to the binding nucleic acid molecule; and nucleic acid monomers released by treating the non-complex fraction with the nuclease is treated with an enzyme and this enzyme reaction is detected. Regarding the analysis method of Embodiment 1B, reference can be made to the above description concerning Embodiment 1A.

In Embodiment 1B, the non-complex fraction contains unreacted binding nucleic acid molecules that have not been involved in the complex formation. Therefore, by treating the unreacted binding nucleic acid molecules with a nuclease and detecting nucleic acid monomers released by this nuclease treatment, it is possible to analyze the unreacted binding nucleic acid molecules. If the unreacted binding nucleic acid molecules can be analyzed, the binding nucleic acid molecules that have been involved in the complex formation also can be analyzed from the analysis result. Thus, as a result, the target that has formed the complexes can be analyzed.

In Embodiment 1B, as the binding nucleic acid molecules, it is preferable to use binding nucleic acid molecules each having the addition polynucleotide added thereto. By the addition of the polynucleotide, for example, the number of nucleic acid monomers released from the binding nucleic acid molecules in the complexes can be increased. Because the released nucleic acid monomers serve as a substrate in the enzyme treatment step, the detection sensitivity can be improved further as the number of the released nucleic acid monomers increases. The conditions for the addition polynucleotide are not particularly limited, and reference can be made to the examples thereof given in the description concerning Embodiment 1A.

As in the case of Embodiment 1A, Embodiment 1B also can be described with reference to FIG. 1. The complex fraction and the non-complex fraction are separated in the same manner as in Embodiment 1A. Then, by treating the non-complex fraction with a nuclease, nucleic acid monomers 13' are cleaved from the addition polynucleotides 13 in the unreacted binding nucleic acid molecules 12, as shown on the right in (D) in FIG. 1. Then, these nucleic acid monomers 13' are treated with an enzyme in the same manner as in Embodiment 1A, and the enzyme reaction is detected. Thus, the target in the sample can be analyzed indirectly.

Regarding Embodiments 1A and 1B, FIG. 1 shows an example where the binding nucleic acid molecules 12 have the addition polynucleotides 13. However, Embodiment 1B is not limited to this illustrative example. For example, the binding nucleic acid molecules 12 may be nucleic acid molecules without the addition polynucleotides 13.

Next, Embodiment 1C of the present invention is directed to an aspect where binding nucleic acid molecules carried on a carrier(s) are used as the binding nucleic acid molecules. Other configurations are the same as those in Embodiment 1A and 1B, for example.

In Embodiment 1C, the number of binding nucleic acid molecules carried on the carrier is not particularly limited. The carrier may carry one binding nucleic acid molecule, or may carry two or more binding nucleic acid molecules. Preferably, the carrier carries a plurality of binding nucleic acid molecules, because the amount of nucleic acid monomers to be released by the nuclease treatment can be increased.

The carrier may carry only a binding nucleic acid molecule(s), or further may carry a polynucleotide(s), for example, because the amount of nucleic acid monomers to be released by the nuclease treatment can be increased. The polynucleotide is not particularly limited, and examples thereof include those given as examples of the polynucleotide in Embodiment 1A.

The carrier is not particularly limited, and examples thereof include the above-described carriers. Among them, beads are preferable.

Regarding Embodiment 1C, an example where binding nucleic acid molecules carried on carriers are used will be described with reference to FIG. 2. FIG. 2 is a schematic view showing the outline of Embodiment 1C of the present invention, and (A) to (D) show the respective steps. It is to be noted that FIG. 2 is a schematic view, and the conditions such as the sizes of a target, binding nucleic acid molecules, addition polynucleotides, and the like, are not limited to those shown in FIG. 2, for example.

In Embodiment 1C, in the complex formation step, a sample containing a target 11 is brought into contact with carriers 20, as shown in (A) in FIG. 2. Each of the carriers 20 carries a plurality of binding nucleic acid molecules 12 and a plurality of polynucleotides 13. As a result, as shown in (B) in FIG. 2, in a reaction solution in the complex formation step, the target 11 in the sample forms complexes with the binding nucleic acid molecules 12 carried on the carriers 20. At this time, unreacted binding nucleic acid molecules 12 that have not been involved in the complex formation also are present in the reaction solution. Subsequent processes are the same as those in Embodiments 1A and 1B.

As shown in FIG. 2, each of the carriers 20 carries a plurality of binding nucleic acid molecules 12 and a plurality of polynucleotides 13. Thus, for example, a large number of nucleic acid monomers can be released by treating the complex fraction with a nuclease as in Embodiment 1A or treating the non-complex fraction with a nuclease as in Embodiment 1B. Thus, analysis with higher sensitivity becomes possible.

(2) Embodiment 2

As described above, Embodiment 2 of the present invention is directed to an aspect where the complex fraction and the non-complex fraction are not separated after the complex formation step, and the reaction system in the complex formation step is subjected to a nuclease treatment.

That is, the analysis method of Embodiment 2 includes: a complex formation step of causing binding nucleic acid molecules that bind to a target and a sample to come into contact with each other to form complexes of the binding nucleic acid molecules and the target in the sample; a nuclease treatment step of releasing nucleic acid monomers from a reaction system for the complex formation by a nuclease treatment; an enzyme treatment step of reacting the released nucleic acid monomers with an enzyme for which the nucleic acid monomers are a substrate; a detection step of detecting the enzyme reaction; and an analysis step of analyzing a target that has formed the complexes from the result of detecting the enzyme reaction.

In Embodiment 2, the nuclease treatment is performed with respect to a reaction system in which the complexes and unreacted binding nucleic acid molecules that have not been involved in the complex formation are present. If the binding nucleic acid molecule forms a complex with the target, the binding nucleic acid molecule in the complex becomes less liable to be degraded by the nuclease owing to physical obstruction. Thus, in the nuclease treatment of the reaction system, nucleic acid monomers are not released from the binding nucleic acid molecules bound to the target by the nuclease, and nucleic acid monomers are released only from the unreacted binding nucleic acid molecules that have not been involved in the complex formation. Therefore, in Embodiment 2, it is not necessary to separate the complex fraction and the non-complex fraction. By releasing the nucleic acid monomers only from the unreacted binding nucleic acid molecules and detecting the released nucleic acid monomers, it is possible to analyze the unreacted binding nucleic acid molecules. If the unreacted binding nucleic acid molecules can be analyzed, the binding nucleic acid molecules that have been involved in the complex formation also can be analyzed from the analysis result. Thus, as a result, the target that has formed the complexes can be analyzed.

In the present embodiment, it is preferable to use the binding nucleic acid molecules without the addition polynucleotides. In the case where the binding nucleic acid molecules each having the addition polynucleotide are used, the length of the addition polynucleotide is not particularly limited, and the upper limit thereof is, for example, 5 bases, 3 bases, or 1 base.

(3) Embodiment 3

As described above, Embodiment 3 of the present invention is directed to an aspect where hybrids each composed of the binding nucleic acid molecule and a single-stranded nucleic acid molecule including a sequence complementary to the binding nucleic acid molecule are used. For instance, Embodiments 3A and 3B to be described below are given as examples.

First, Embodiment 3A of the present invention is directed to an aspect where, as described above, the binding nucleic acid molecules are each in the form of a hybrid with the single-stranded nucleic acid molecule including a sequence complementary to the binding nucleic acid molecule. Specifically, the analysis method of Embodiment 3A includes: a complex formation step of causing the hybrids and a sample to come into contact with each other to form complexes of the binding nucleic acid molecules in the hybrids and a target in the sample and to release the single-stranded nucleic acid molecules from the hybrids; a nuclease treatment step of releasing nucleic acid monomers from a reaction system for the complex formation by a nuclease treatment; an enzyme treatment step of reacting the released nucleic acid monomers with an enzyme for which the nucleic acid monomers are a substrate; a detection step of detecting the enzyme reaction; and an analysis step of analyzing the target that has formed the complexes from the result of detecting the enzyme reaction.

In Embodiment 3A, by using a nuclease for which the single-stranded nucleic acid is a substrate in the nuclease treatment step, it is possible to release the nucleic acid monomers from single-stranded nucleic acid molecules released from the hybrids, without releasing nucleic acid monomers from the complexes. Then, by treating the released single-stranded nucleic acid molecules with a nuclease and detecting nucleic acid monomers released by this nuclease treatment, it is possible to analyze the single-stranded nucleic acid molecules released from the hybrids. If the released single-stranded nucleic acid molecules can be analyzed, the binding nucleic acid molecules that have been involved in the complex formation also can be analyzed from the analysis result. Thus, as a result, the target that has formed the complexes can be analyzed.

For the single-stranded nucleic acid molecule, it is only required that the single-stranded nucleic acid molecule have a sequence complementary to the binding nucleic acid molecule and can hybridize to the binding nucleic acid molecule. The length of the single-stranded nucleic acid molecule is not particularly limited, and can be set as appropriate depending on the binding nucleic acid molecule. The ratio between the length of the binding nucleic acid molecule and the length of the single-stranded nucleic acid molecule is not particularly limited. For example, the single-stranded nucleic acid molecule may have a length corresponding to 1/1 to 1/1000 of the length of the binding nucleic acid molecule. The single-stranded nucleic acid molecule may be bound to any region in the binding nucleic acid molecule.

The nuclease used in Embodiment 3 may be, as described above, a nuclease for which the single-stranded nucleic acid is a substrate.

Figure 3A:
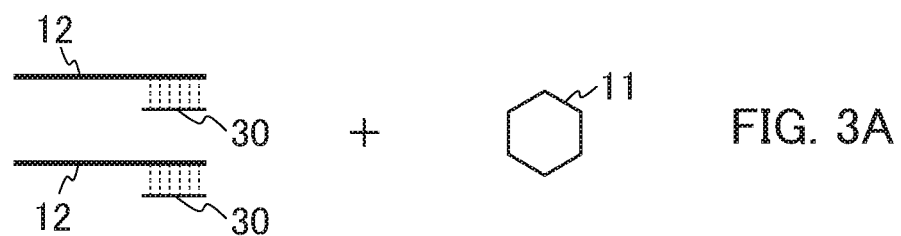
FIG. 3 is a schematic view showing still another example of the analysis method of the present invention.
Figure 3B:
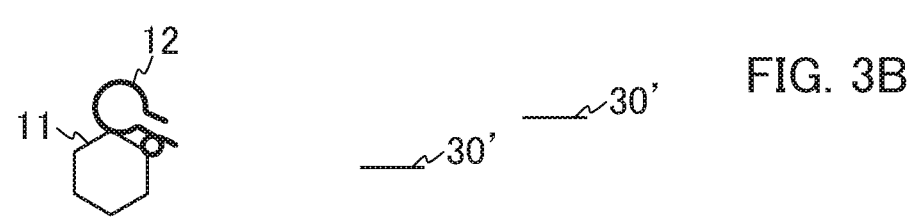
Figure 3C:
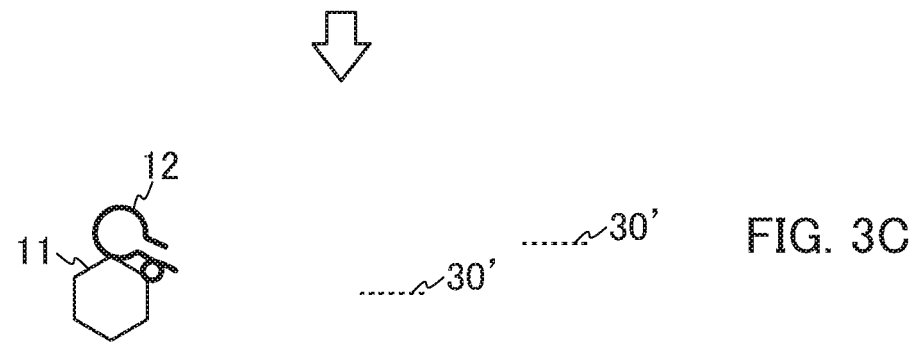

Regarding Embodiment 3A, an example where hybrids each composed of the binding nucleic acid molecule and the single-stranded nucleic acid molecule are used will be described with reference to FIG. 3. FIG. 3 is a schematic view showing the outline of Embodiment 3 of the present invention. It is to be noted that FIG. 3 is a schematic view, and the conditions such as the sizes of a target, binding nucleic acid molecules, single-stranded nucleic acid molecules, and the like, are not limited to those shown in FIG. 3, for example.

In Embodiment 3A, in the complex formation step, as shown in (A) in FIG. 3, a sample containing a target 11 is brought into contact with hybrids each composed of a binding nucleic acid molecule 12 and a single-stranded nucleic acid molecule 30. As a result, as shown in (B) in FIG. 3, in the reaction solution in the complex formation step, the binding nucleic acid molecules 12 in the hybrids bind to the target 11 in the sample, whereby the single-stranded nucleic acid molecules 30 in the hybrids are released. Then, the reaction solution containing the complexes and the released single-stranded nucleic acid molecules 30 is treated with a nuclease for which the single-stranded nucleic acid is a substrate, whereby, as shown in (C) in FIG. 3, nucleic acid monomers are not released from the complexes and nucleic acid monomers 30' are cleaved only from the single-stranded nucleic acid molecules 30. Then, the nucleic acid monomers 30' released from the single-stranded nucleic acid molecules 30 are treated with an enzyme, and the enzyme reaction is detected. Thus, it is possible to detect the released single-stranded nucleic acid molecules 30, whereby the target in the sample can be analyzed indirectly.

Next, Embodiment 3B is directed to an aspect where the hybrids are carried on a carrier(s). The analysis method of Embodiment 3B is the same as the analysis method of Embodiment 3A, except that: the hybrids carried on the carrier(s) are used; after the complex formation step, a solid fraction containing the carrier(s) and a liquid fraction are separated; and the liquid fraction is subjected to the nucleotide treatment and the enzyme treatment.

In Embodiment 3B, the solid fraction, i.e., a fraction containing the carriers, contains carriers with the binding nucleic acid molecules carried thereon being bound to the target to form complexes and unreacted carriers with the binding nucleic acid molecules carried thereon not being bound to the target. On the other hand, the liquid fraction contains released single-stranded nucleic acid molecules. Thus, by treating the liquid fraction with a nuclease to release nucleic acid monomers, treating the released nucleic acid monomers with an enzyme, and detecting the enzyme reaction, it is possible to analyze the single-stranded nucleic acid molecules released from the hybrids. If the released single-stranded nucleic acid molecules can be analyzed, the binding nucleic acid molecules that have been involved in the complex formation also can be analyzed from the analysis result. Thus, as a result, the target that has formed the complexes can be analyzed.

Figure 4A:
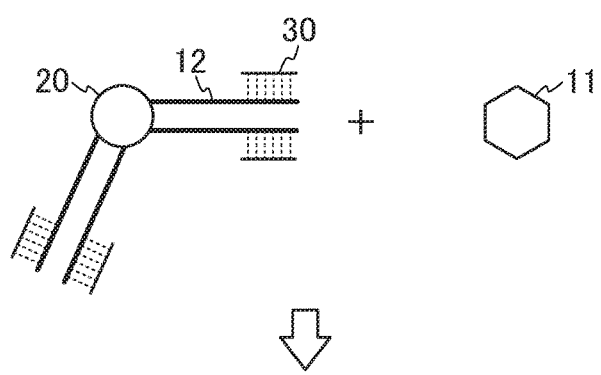
FIG. 4 is a schematic view showing yet another example of the analysis method of the present invention.
Figure 4B:
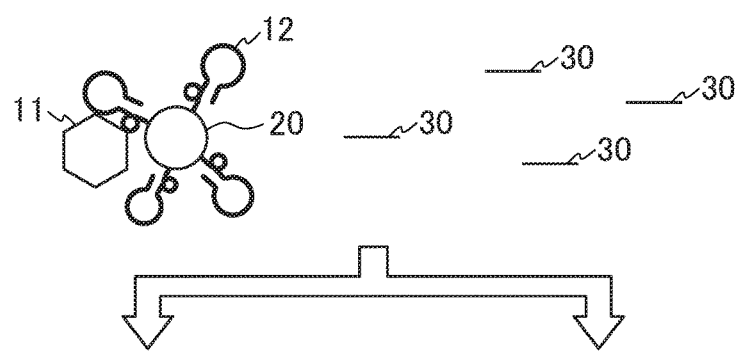
Figure 4C:
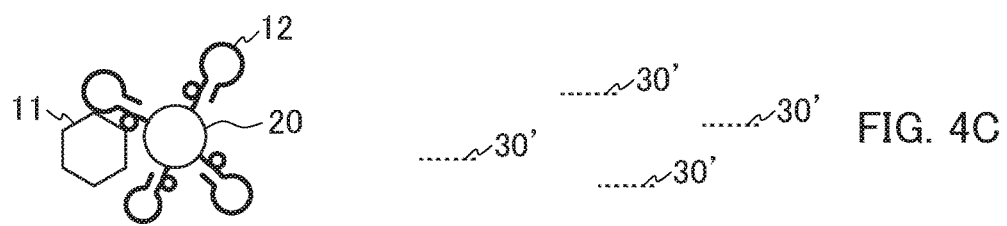

Regarding Embodiment 3B, an example where carriers carrying hybrids each composed of the binding nucleic acid molecule and the single-stranded nucleic acid molecule are used will be described with reference to FIG. 4. FIG. 4 is a schematic view showing the outline of Embodiment 3B of the present invention. It is to be noted that FIG. 4 is a schematic view, and the conditions such as the sizes of a target, binding nucleic acid molecules, single-stranded nucleic acid molecules, and the like, are not limited to those shown in FIG. 4, for example.

In Embodiment 3B, in the complex formation step, as shown in (A) in FIG. 4, a sample containing a target 11 is brought into contact with carriers 20 each carrying hybrids of binding nucleic acid molecules 12 and single-stranded nucleic acid molecules 30. As a result, as shown in (B) in FIG. 4, in the reaction solution in the complex formation step, the binding nucleic acid molecules 12 in the hybrids bind to the target 11 in the sample, whereby the single-stranded nucleic acid molecules 30 in the hybrids are released. Next, the reaction solution is separated into a solid fraction containing the carriers 20 and a liquid fraction containing the released single-stranded nucleic acid molecules 30. Then, the released single-stranded nucleic acid molecules 30 are treated with a nuclease, whereby, as shown in (D) in FIG. 4, nucleic acid monomers 30' are cleaved from the single-stranded nucleic acid molecules 30. Then, the nucleic acid monomers 30' released from the single-stranded nucleic acid molecules 30 are treated with an enzyme, and the enzyme reaction is detected. Thus, it is possible to detect the released single-stranded nucleic acid molecules 30, whereby the target in the sample can be analyzed indirectly.

(Target Analysis Kit)

The target analysis kit of the present invention is an analysis kit for use in the analysis method according to the present invention, including: a binding nucleic acid molecule that binds to a target; a nuclease; and an enzyme for which a nucleic acid monomer is a substrate. According to the analysis kit of the present invention, the analysis method of the present invention can be carried out easily. Regarding the analysis kit of the present invention, reference can be made to the above description concerning the analysis method of the present invention.

EXAMPLES

Next, examples of the present invention will be described. It is to be noted, however, that the present invention is by no means limited by the following examples. Unless otherwise stated, commercially available reagents were used in accordance with their protocols.

Example 1

Nucleic acid monomers were released from nucleic acid molecules by a nuclease treatment, and the released nucleic acid monomers were detected using luciferase.

As the nucleic acid molecule, DNA consisting of the base sequence of the following SEQ ID NO: 1 (N30-079) was used.

N30-079

(SEQ ID NO: 1)
5'-GGATTGAACGCCGCCCTTATAAACNNNNNNNNNNNNNNNNNNNNNNNN
NNNNNNNCATCAGGTCCAGTGCTCTCGTATAG-3'

The nucleic acid molecules and DNA endonuclease (trade name BAL31 Nuclease, TAKARA) were mixed together at the proportion shown in Table 1 below. The mixture was incubated at 30° C. for 30 minutes, thereby releasing nucleic acid monomers from the nucleic acid molecules.

TABLE 1

(Nuclease treatment condition)

| Nucleic acid molecule | Final concentration: 1 μmol/L |
|---|---|
| BAL31 Nuclease | 10 units |
| 2 × BAL Buffer | 10 μL |
| Total | 20 μL |

The reaction solution after the nuclease treatment was diluted with ultrapure water to achieve a predetermined dilution factor ($10^1$-fold, $10^2$-fold, $10^3$-fold, $10^4$-fold, or $10^5$-fold). Thus, diluted samples were prepared. Then, each of the diluted samples was supplied to an AMP test kit (trade name: LuciPac® Pen, Kikkoman Corporation), and the relative light units of the diluted sample were measured using a measurement device (trade name: Lumitester PD-20, Kikkoman Corporation). As a negative control, the relative light units were measured in the same manner, except that 1 μmol/L N30-079 was not treated with the nuclease. Also, as a control, the relative light units were measured in the same manner (N=3), except that the 2×BAL buffer was used instead of the nucleic acid molecules.

Figure 5:
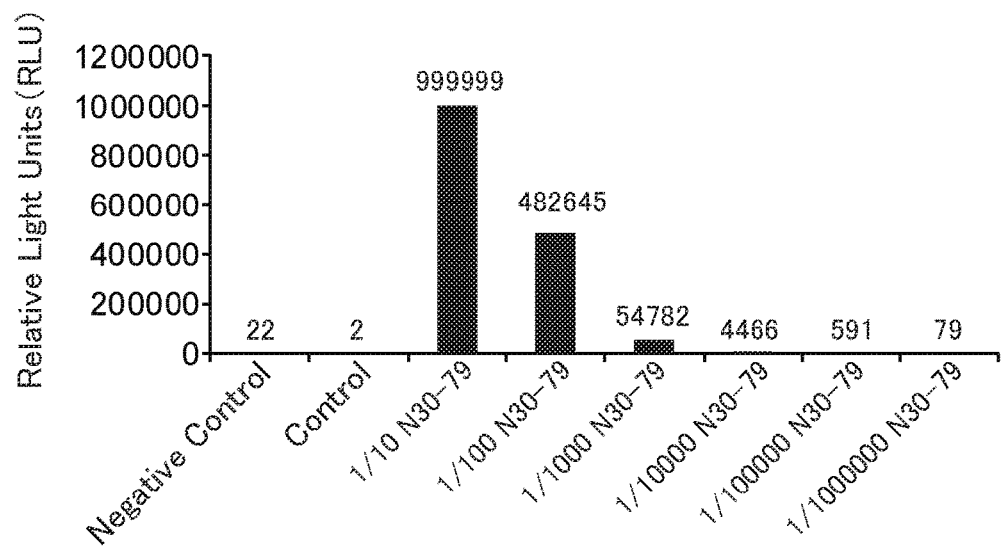
FIG. 5 is a graph showing the amount of light emission in Example 1.

The results obtained are shown in FIG. 5. FIG. 5 is a graph showing the relative light units. In FIG. 5, the horizontal axis indicates the type of the sample, and the vertical axis indicates the relative light units. Numerical values shown in the graph indicate the relative light units of the respective samples. As can be seen from FIG. 5, in the negative control and the control, light emission was not measured. In contrast, in the diluted samples, strong light emission was measured when the nucleic acid molecules at any concentration were used. From these results, it was found that light emission can be measured by releasing nucleic acid monomers from nucleic acid molecules through a nuclease treatment and reacting the released nucleic acid monomers with an enzyme for which nucleic acid monomers are a substrate.

Example 2

By allowing a nuclease and luciferase to be present together, release of nucleic acid monomers from nucleic acid molecules and detection of the released nucleic acid monomers were carried out at the same time.

A sample was prepared by mixing N30-079 and the above-described DNA endonuclease at the same proportion shown in Table 1 above, except that the amount of the DNA endonuclease was set to 1 unit. Next, the sample was supplied to the AMP test kit, and was allowed to stand still for 20 minutes. Then, using the above-described measurement device, the relative light units of the sample were measured every 15 seconds.

Figure 6:
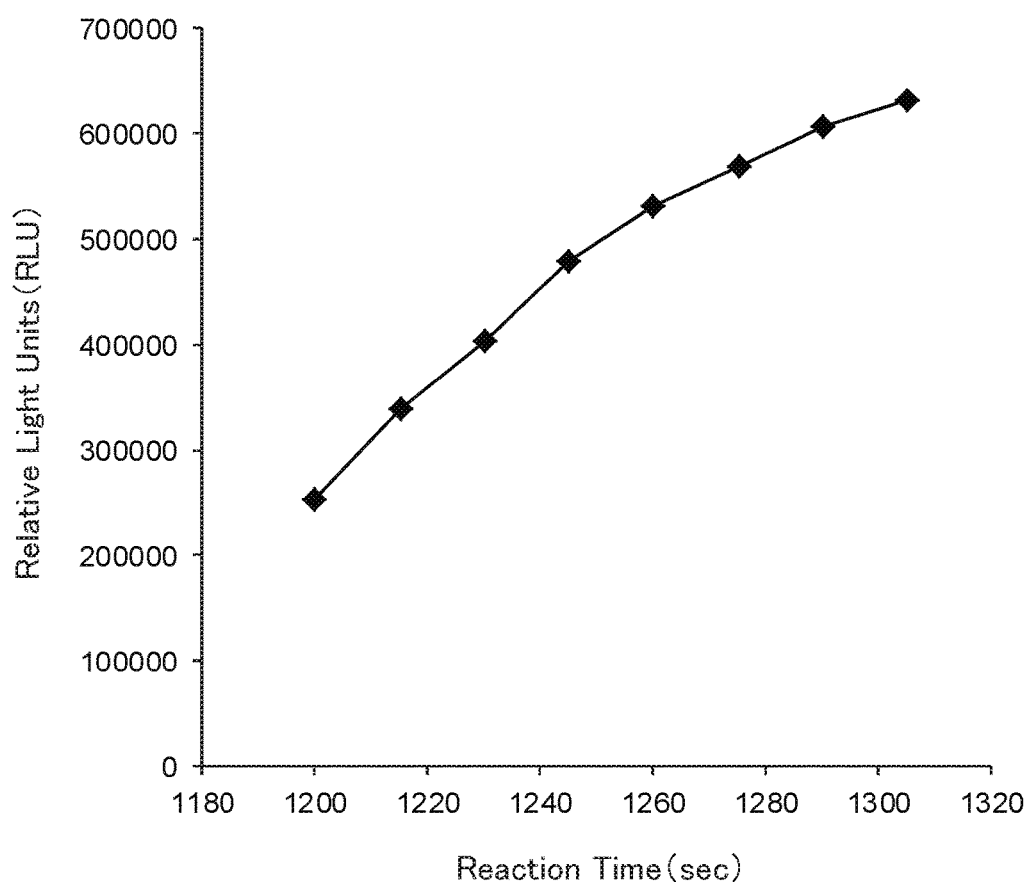
FIG. 6 is a graph showing the amount of light emission in Example 2.

The results obtained are shown in FIG. 6. FIG. 6 is a graph showing the relative light units. In FIG. 6, the horizontal axis indicates the reaction time, and the vertical axis indicates the relative light units. It is to be noted that the reaction time indicates the time period elapsed from the addition of the sample to the AMP test kit. As can be seen from FIG. 6, strong light emission was measured under any reaction time. From these results, it was found that it is possible to detect nucleic acid molecules even when the nuclease treatment step and the enzyme treatment step are performed at the same time.

Example 3

Complexes of binding nucleic acid molecules (aptamers) that bind to hemagglutinin (HA) in influenza viruses and HA were formed, and nucleic acid monomers were released from the complexes by a nuclease treatment. Then, the released nucleic acid monomers were detected using luciferase.

As an aptamer (RHA0006) that binds to HA in influenza viruses, DNA consisting of the base sequence of the following SEQ ID NO: 2 was used. The aptamer was adapted so as to include 24-mer poly(dA) added to the 3' end thereof. Next, the aptamers were added to a TBS buffer at a concentration of 100 nmol/L. The composition of the TBS buffer was 50 mmol/L Tris-HCl, 100 mmol/L NaCl, 5 mmol/L KCl, 1 mmol/L $MgCl_2$, and 0.05% Tween® 20, and the pH of the TBS buffer was 7.4. Then, the aptamer solution was heat-treated at 95° C. for 5 minutes, and further was allowed to stand still on ice for 5 minutes.

RHA0006

(SEQ ID NO: 2)
5'-GGGTTTGGGTTGGGTTGGGTTTTTGGGTTTGGGTTGGGTTGGGAA
AAAAAAAAAAAAAAAAAAAAAAAA-3'

Next, as HA, influenza virus (H5N1)-derived HA was used. The HA was diluted with a TBS buffer so as to achieve a predetermined HA concentration (0, $10^1$, $10^2$, $10^3$, $10^4$, or $10^5$ pmol/L). Thus, diluted samples were prepared.

Each of the diluted samples was added to a 96-well plate (trade name: Nunc-Immuno® plate, Maxisorp®, manufactured by Nunc) so that each well contained 100 μL of the diluted sample, and the diluted sample was adsorbed to the wells at 4° C. for 16 hours. The wells were washed three times with 200 μL of the TBS buffer. Thereafter, 200 μL of a Protein Free (TBS) Blocking Buffer (manufactured by Pierce) was added to the wells, and the mixture was incubated at room temperature for 1 hour. After the incubation, 100 μL of the aptamer solution after the still standing was added to the wells, and the mixture was incubated at room temperature for 30 minutes. Then, the wells were washed three times with 200 μL of the TBS buffer.

Next, BAL31 Nuclease was added to the plate so that each well contained 20 μL (3 units/well) of the BAL31 Nuclease, and the mixture was incubated at room temperature for 20 minutes. After the incubation, the solution in the wells was added to the AMP test kit, and the relative light units were measured in the same manner as in Example 1 (N=3).

Figure 7:
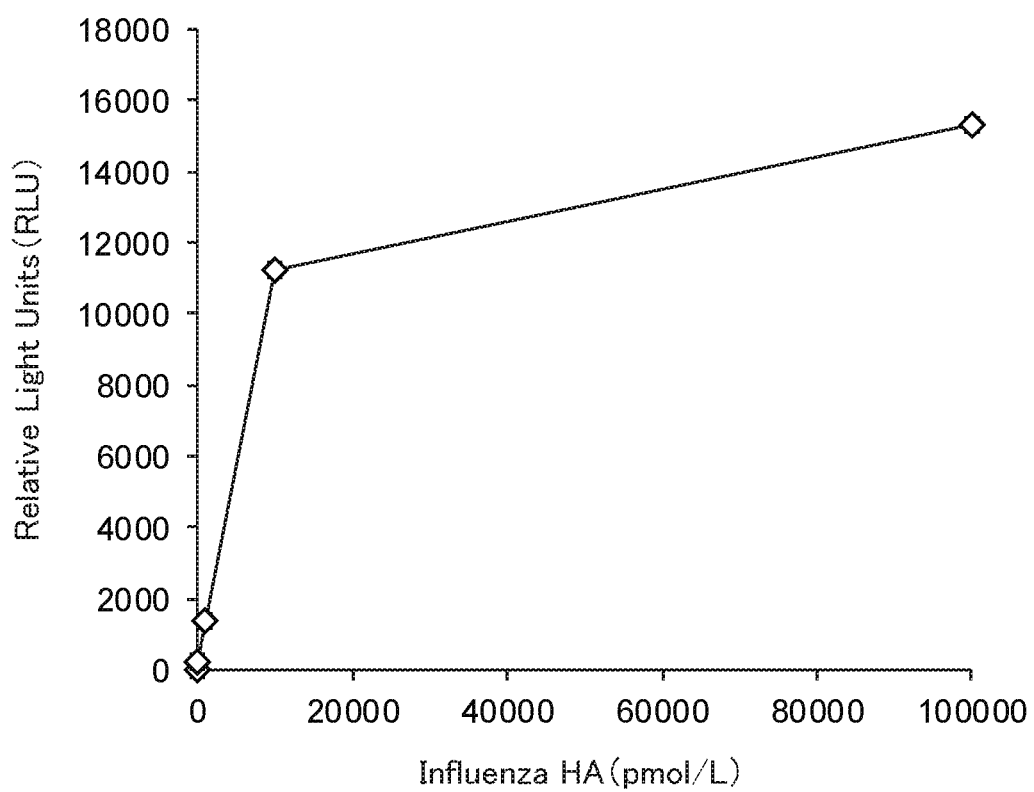
FIG. 7 is a graph showing the amount of light emission in Example 3.

The results obtained are shown in FIG. 7. FIG. 7 is a graph showing the relative light units. In FIG. 7, the horizontal axis indicates the HA concentration in the diluted samples, and the vertical axis indicates the relative light units. As can be seen from FIG. 7, light emission was not measured when the diluted sample with the HA concentration of 0 pmol/L was used. In contrast, light emission was measured when the diluted sample with any of the HA concentrations was used. From these results, it was found that light emission can be measured by treating a fraction of complexes of binding nucleic acid molecules and a target with a nuclease to release nucleic acid monomers from the nucleic acid molecules and reacting the released nucleic acid monomers with an enzyme for which the nucleic acid monomers are a substrate.

While the present invention has been described above with reference to exemplary embodiments, the present invention is by no means limited thereto. Various changes and modifications that may become apparent to those skilled in the art may be made in the configuration and specifics of the present invention without departing from the scope of the present invention.

This application is based upon and claims the benefit of priority from Japanese Patent Application No. 2013-205051 filed on Sep. 30, 2013, the disclosure of which is incorporated herein its entirety by reference.

INDUSTRIAL APPLICABILITY

According to the present invention, it is possible to detect a target easily by forming complexes of the target and the binding nucleic acid molecules, releasing nucleic acid monomers from a complex fraction or a non-complex fraction, and performing an enzyme reaction with the released nucleic acid monomers as a substrate. According to this method, for example, it is not necessary to link a DNAzyme to aptamers as described above, so that the ON-OFF control of the catalytic ability of the DNAzyme depending on the presence or absence of a target also is not necessary. Also, according to the analysis kit of the present invention, the analysis method of the present invention can be carried out easily. Because the present invention relates to a target detection method using aptamers, it can be said that the present invention is a very useful technique for research and tests in various fields such as clinical medical practice, foods, and environments, for example.

[Sequence Listing] TF14015WO_2014.05.20_ST25.txt

The invention claimed is:

1. An analysis method for analyzing a target, the analysis method comprising:
   a complex formation step of causing a binding nucleic acid molecule that binds to the target and a sample to come into contact with each other to form a complex of the binding nucleic acid molecule and the target in the sample;
   a nuclease treatment step of releasing a nucleic acid monomer from at least one of a complex fraction and a non-complex fraction by a nuclease treatment;
   an enzyme treatment step of reacting the released nucleic acid monomer with an enzyme for which the nucleic acid monomer is a substrate;
   a detection step of detecting the enzyme reaction; and
   an analysis step of analyzing the target that has formed the complex from the result of detecting the enzyme reaction, wherein
   the nuclease is an exonuclease.

2. The analysis method according to claim 1, further comprising, after the complex formation step, a separation step of separating the complex fraction and the non-complex fraction from a reaction system for the complex formation.

3. The analysis method according to claim 2, wherein
   in the separation step, the complex fraction and the non-complex fraction are separated by causing the reaction system for the complex formation and an immobilized binding substance to come into contact with each other to bind the complex to the binding substance, and
   the binding substance is a binding substance that binds to the target.

4. The analysis method according to claim 3, wherein
   in the separation step, after the complex has been bound to the binding substance, the immobilized binding substance is washed to remove an unreacted binding nucleic acid molecule.

5. The analysis method according to claim 2, wherein
   in the nuclease treatment step, the complex fraction is subjected to the nuclease treatment to release the nucleic acid monomer from the complex.

6. The analysis method according to claim 2, wherein
   in the nuclease treatment step, the non-complex fraction is subjected to the nuclease treatment to release the nucleic acid monomer from an unreacted binding nucleic acid molecule.

7. The analysis method according to claim 1, wherein
   the binding nucleic acid molecule comprises a polynucleotide added thereto, and
   the polynucleotide comprises a nucleic acid monomer that is the substrate for the enzyme.

8. The analysis method according to claim 1, wherein the binding nucleic acid molecule is carried on a carrier.

9. The analysis method according to claim 8, wherein
the carrier further comprises a polynucleotide added thereto, and
the polynucleotide comprises a nucleic acid monomer that is the substrate for the enzyme.

10. The analysis method according to claim 1, wherein
in the nuclease treatment step, the reaction system in the complex formation step is subjected to the nuclease treatment to release the nucleic acid monomer from an unreacted binding nucleic acid molecule.

11. The analysis method according to claim 1, wherein
the binding nucleic acid molecule is in a form of a hybrid with a single-stranded nucleic acid molecule comprising a sequence complementary to the binding nucleic acid molecule,
in the complex formation step, the hybrid and the sample are caused to come into contact with each other to form a complex of the binding nucleic acid molecule in the hybrid and the target and to release the single-stranded nucleic acid molecule from the hybrid, and
in the nuclease treatment step, the reaction system in the complex formation step is subjected to the nuclease treatment to release the nucleic acid monomer from the released single-stranded nucleic acid molecule.

12. The analysis method according to claim 1, wherein
the binding nucleic acid molecule is carried on a carrier and is in a form of a hybrid with a single-stranded nucleic acid molecule comprising a sequence complementary to the binding nucleic acid molecule,
in the complex formation step, the hybrid and the sample are caused to come into contact with each other to form a complex of the binding nucleic acid molecule in the hybrid and the target and to release the single-stranded nucleic acid molecule from the hybrid, and
in the nuclease treatment step, the reaction system in the complex formation step is subjected to the nuclease treatment to release the nucleic acid monomer from the released single-stranded nucleic acid molecule.

13. The analysis method according to claim 12, further comprising, after the complex formation step, a separation step of separating the released single-stranded nucleic acid molecule from a reaction system in the complex formation step,
wherein, in the nuclease treatment step, the separated single-stranded nucleic acid molecule is subjected to the nuclease treatment to release the nucleic acid monomer from the single-stranded nucleic acid molecule.

14. The analysis method according to claim 11, wherein the nuclease is a nuclease for which the single-stranded nucleic acid molecule is a substrate.

15. The analysis method according to claim 1, wherein the nucleic acid monomer as a substrate for the enzyme is an adenosine nucleotide.

16. The analysis method according to claim 15, wherein the adenosine nucleotide is at least one of ribonucleotide and deoxyribonucleotide.

17. The analysis method according to claim 1, wherein the enzyme is a protein having luciferase activity.

18. The analysis method according to claim 1, wherein the enzyme is luciferase.

19. The analysis method according to claim 1, wherein
in the enzyme treatment step, the enzyme reaction is performed in the presence of a reagent, and
the reagent is a reagent that causes a signal to be generated by an enzyme reaction with the nucleic acid monomer as a substrate or a reagent that causes a signal to disappear by an enzyme reaction with the nucleic acid monomer as a substrate.

20. The analysis method according to claim 1, wherein
in the detection step, a signal generated by the enzyme reaction or a signal caused to disappear by the enzyme reaction is detected.

21. The analysis method according to claim 19, wherein the signal is at least one of an optical signal and an electrical signal.

22. The analysis method according to claim 8, wherein the carrier is a bead or a plate.

23. An analysis kit for use in the analysis method according to claim 1, the analysis kit comprising:
a binding nucleic acid molecule that binds to a target;
a nuclease; and
an enzyme for which a nucleic acid monomer is a substrate.

24. The analysis kit according to claim 23, wherein
the binding nucleic acid molecule comprises a polynucleotide added thereto, and
the polynucleotide comprises a nucleic acid monomer that is the substrate for the enzyme.

25. The analysis kit according to claim 23, wherein the binding nucleic acid molecule is carried on a carrier.

26. The analysis kit according to claim 25, wherein
the carrier further comprises a polynucleotide added thereto, and
the polynucleotide comprises a nucleic acid monomer that is the substrate for the enzyme.

27. The analysis kit according to claim 23, wherein
the binding nucleic acid molecule is in a form of a hybrid with a single-stranded nucleic acid molecule comprising a sequence complementary to the binding nucleic acid molecule, and
through contact with the target, the binding nucleic acid molecule in the hybrid forms a complex with the target and the single-stranded nucleic acid molecule is released.

28. The analysis kit according to claim 27, wherein the nuclease is a nuclease for which the single-stranded nucleic acid molecule is a substrate.

29. The analysis kit according to claim 23, wherein
the binding nucleic acid molecule is carried on a carrier and is in a form of a hybrid with a single-stranded nucleic acid molecule comprising a sequence complementary to the binding nucleic acid molecule, and
through contact with the target, the binding nucleic acid molecule in the hybrid forms a complex with the target and the single-stranded nucleic acid molecule is released.

30. The analysis kit according to claim 23, wherein the nuclease is an exonuclease.

31. The analysis kit according to claim 23, wherein the nucleic acid monomer as a substrate for the enzyme is an adenosine nucleotide.

32. The analysis kit according to claim 31, wherein the adenosine nucleotide is at least one of ribonucleotide and deoxyribonucleotide.

33. The analysis kit according to claim 23, wherein the enzyme is a protein having luciferase activity.

34. The analysis kit according to claim 23, wherein the enzyme is luciferase.

35. The analysis kit according to claim 23, further comprising a reagent, wherein
the reagent is a reagent that causes a signal to be generated by an enzyme reaction with the monomer as a substrate or a reagent that causes a signal to disappear by an enzyme reaction with the monomer as a substrate.

36. The analysis kit according to claim 35, wherein the signal is at least one of an optical signal and an electrical signal.

37. The analysis kit according to claim 25, wherein the carrier is a bead or a plate.

* * * * *